United States Patent
Ramee et al.

(10) Patent No.: US 10,321,933 B1
(45) Date of Patent: Jun. 18, 2019

(54) APPARATUS AND METHODS FOR VASCULAR ACCESS

(71) Applicant: MarVenRay, LLC, Metairie, LA (US)

(72) Inventors: Stephen R. Ramee, Metairie, LA (US); Lodovico Marziale, New Orleans, LA (US); Laurie Ventura, Metairie, LA (US)

(*) Notice: Subject to any disclaimer, the term of this patent is extended or adjusted under 35 U.S.C. 154(b) by 719 days.

(21) Appl. No.: 14/662,146

(22) Filed: Mar. 18, 2015

Related U.S. Application Data

(60) Provisional application No. 62/071,451, filed on Sep. 24, 2014.

(51) Int. Cl.
| | |
|---|---|
| *A61B 17/34* | (2006.01) |
| *A61B 17/02* | (2006.01) |
| *A61M 29/00* | (2006.01) |
| *A61B 17/00* | (2006.01) |

(52) U.S. Cl.
CPC ...... *A61B 17/3423* (2013.01); *A61B 17/0218* (2013.01); *A61B 17/3498* (2013.01); *A61M 29/00* (2013.01); *A61B 2017/00292* (2013.01); *A61B 2017/347* (2013.01); *A61B 2017/3449* (2013.01)

(58) Field of Classification Search
CPC ............ A61B 17/3417; A61B 17/3423; A61B 17/0218; A61M 39/06
See application file for complete search history.

(56) References Cited

U.S. PATENT DOCUMENTS

| | | | | |
|---|---|---|---|---|
| 2012/0271236 | A1* | 10/2012 | Bruszewski | A61M 39/0606 604/167.03 |
| 2015/0038994 | A1* | 2/2015 | Prior | A61M 5/329 606/147 |
| 2016/0045220 | A1* | 2/2016 | Wachli | A61B 17/3423 600/204 |
| 2016/0045224 | A1* | 2/2016 | Hendershot, III | A61B 17/3474 604/26 |
| 2017/0232236 | A1* | 8/2017 | Al-Rashdan | A61M 29/00 604/96.01 |

* cited by examiner

*Primary Examiner* — Olivia C Chang
(74) *Attorney, Agent, or Firm* — William A. English; Vista IP Law Group LLP

(57) ABSTRACT

Apparatus and methods are provided for performing a medical procedure using an introducer sheath and a plurality of valve hubs. The introducer sheath includes a lumen extending between proximal and distal portions and a hub on the proximal portion. Each valve hub includes a valve body including a plurality of ports. The valve hubs may include different numbers and/or configurations of ports to facilitate introducing multiple instruments simultaneously through the tubular member. Optionally, the kit may also include one or more dilators. Each valve hub and the dilator may include connectors for mating with connectors on the tubular member hub releasably coupling a selected valve hub or the dilator to the tubular member.

19 Claims, 3 Drawing Sheets

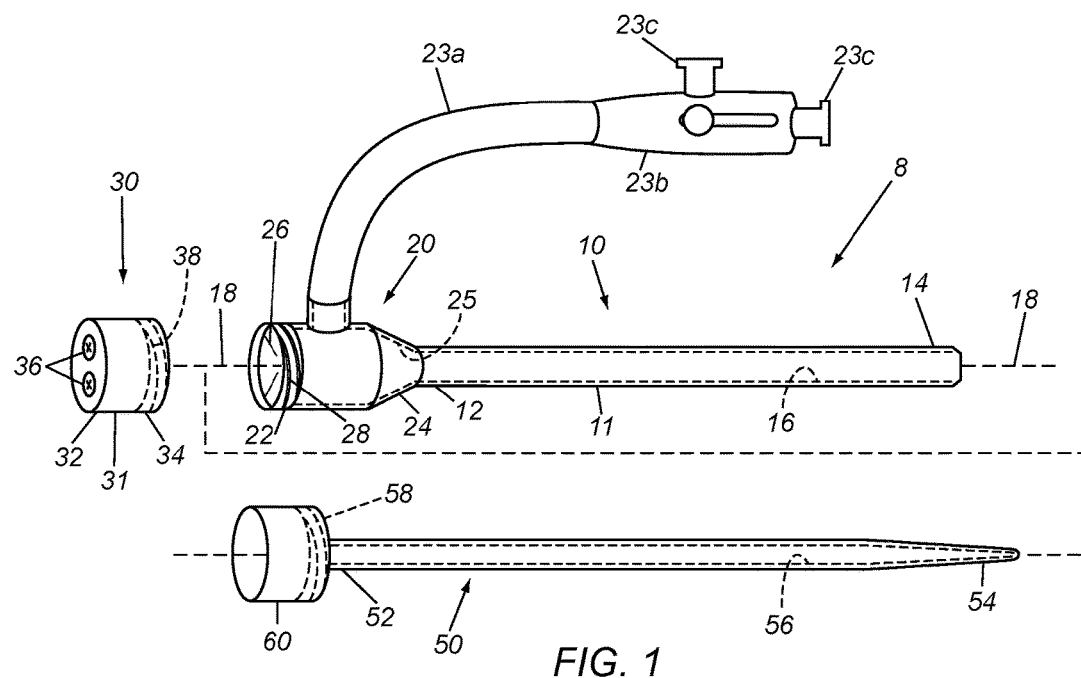
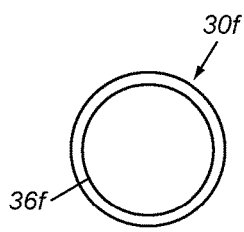
FIG. 4F
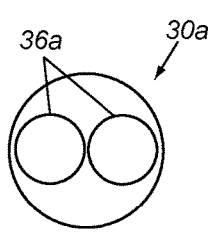
FIG. 4A
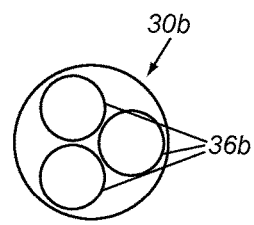
FIG. 4B
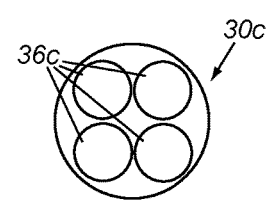
FIG. 4C
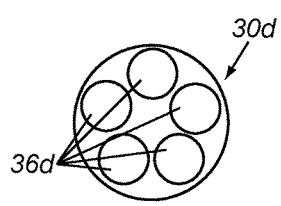
FIG. 4D
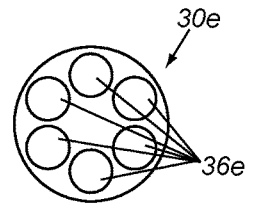
FIG. 4E

APPARATUS AND METHODS FOR VASCULAR ACCESS

This application claims benefit of U.S. provisional application Ser. No. 62/071,451, filed Sep. 20, 2014, the entire disclosure of which is expressly incorporated by reference herein.

FIELD OF THE INVENTION

The present invention relates generally to apparatus and methods for accessing body lumens within a patient's body, e.g., to access the patient's vasculature to deliver one or more instruments during a medical procedure, and, more particularly, to modular access sheaths including valve hubs configured to provide different numbers and/or configurations of access ports using such sheaths, and to methods for making and using such sheaths and valve hubs.

BACKGROUND

There are many medical procedures where one or more guidewires, catheters, sheaths, and/or other medical devices or instruments may be introduced into a patient's body cavity, recess, vessel, organ, and/or other body lumen. In many of these procedures, multiple devices are used and consequently multiple access sites are needed to introduce the instruments.

Generally, during a cardiac, vascular, or other procedure involving the patient's vascular system, an introducer sheath is placed percutaneously into the patient's vasculature, e.g., through the patient's skin into a peripheral artery or vein, such as the femoral artery, carotid artery, or other blood vessel, to provide access into the patient's body. For example, a hollow needle may be inserted through a patient's skin and overlying tissue into a blood vessel. A guide wire may be passed through the needle lumen into the blood vessel, whereupon the needle may be removed.

An introducer sheath may then be advanced over the guide wire into the vessel, e.g., in conjunction with or subsequent to one or more dilators. One or more catheters and/or other instruments may then be advanced individually through the introducer sheath over the guide wire into a position for performing a medical procedure. Thus, the introducer sheath may facilitate accessing and/or introducing various instruments separately into the vessel, while minimizing trauma to the vessel wall and/or minimizing blood loss.

If multiple instruments are needed substantially simultaneously during a procedure, multiple introducer sheaths are generally used, with each introducer sheath placed in different blood vessels to provide access for the devices. If more than one instrument is introduced through a single introducer sheath, e.g., adjacent one another, the seal within the introducer sheath may not provide sufficient hemostasis around the multiple instruments, risking loss of blood, low blood pressure, undesired introduction of air, and/or other potential problems for the patient. The use of multiple sheaths in a vessel may also lead to more risk of bleeding complications from repeated needle access attempts and/or the need for multiple closure devices at the end of the procedure.

Therefore, apparatus and methods that may facilitate delivery of multiple instruments through a single sheath during a medical procedure would be useful.

SUMMARY

The present invention is directed generally to apparatus and methods for accessing body lumens within a patient's body, e.g., to access the patient's vasculature to deliver one or more instruments during a medical procedure. More particularly, the present invention is directed to modular access sheaths including valve hubs configured to provide different numbers and/or configurations of access ports using such sheaths, and to methods for making and using such sheaths.

In accordance with one embodiment, an apparatus is provided for performing a medical procedure within a patient's body that includes an introducer sheath or other tubular member including a proximal portion, a distal portion sized for introduction into a body lumen, a lumen extending between the proximal portion and the distal portion, and a hub on the proximal portion; and a valve hub comprising a valve body including a proximal end and a distal end, a plurality of ports on the proximal end communicating with a single opening in the distal end. Each port may include one or more seals therein for accommodating inserting a device into the port while providing a substantially fluid-tight seal. In addition, cooperating connectors may be provided on the tubular member hub and the valve body for releasably coupling the valve hub to the tubular member hub such that a device inserted into one of the ports enters the tubular member lumen.

Optionally, the apparatus may include a dilator that includes a proximal portion including a hub and a distal portion sized for insertion into the tubular member hub and lumen such that the distal dilator portion extends from an outlet in the tubular member distal portion, the dilator hub including one or more connectors for engaging one or more connectors on the tubular member hub for coupling the dilator to the tubular member.

In accordance with another embodiment, a kit is provided for performing a medical procedure that includes an introducer sheath or other tubular member including a proximal portion, a distal portion sized for introduction into a body lumen, a lumen extending between the proximal portion and the distal portion, and a hub on the proximal portion; and a plurality of valve hubs. Each valve hub may include a valve body including a proximal end and a distal end, a plurality of ports on the proximal end communicating with a single opening in the distal end. Each port may include one or more seals therein for accommodating inserting a device into the port while providing a substantially fluid-tight seal. The valve hubs may include different numbers and/or configurations of ports to facilitate introducing multiple instruments simultaneously through the tubular member.

Optionally, the kit may also include one or more dilators, each including a proximal portion including a hub and a distal portion sized for insertion into the tubular member hub and lumen such that the dilator distal portion extends from an outlet in the tubular member distal portion. Each valve hub and the dilator may include one or connectors for mating with one or more connectors on the tubular member hub for releasably coupling a selected valve hub or the dilator to the tubular member hub.

In accordance with still another embodiment, a method is provided for preparing an introducer sheath that includes providing a tubular member comprising a proximal portion, a distal portion sized for introduction into a body lumen, a lumen extending between the proximal portion and the distal portion, and a hub on the proximal portion; providing a plurality of valve hubs, each valve hub including a valve body including a proximal end and a distal end, a plurality of ports on the proximal end communicating with a single opening in the distal end, each port including one or more seals therein for accommodating inserting a device into the port while providing a substantially fluid-tight seal; selecting a first valve hub from the plurality of the valve hubs having a desired configuration of ports; and coupling the first valve hub to the tubular member hub.

Optionally, the method may also include decoupling the first valve hub from the tubular member hub; selecting a second valve hub having a different configuration of ports than the first valve hub; and coupling the second valve hub to the tubular member hub.

In accordance with yet another embodiment, a method is provided for performing a medical procedure within a patient's body that includes providing a tubular member including a proximal portion, a distal portion, a lumen extending between the proximal and distal portions, and a hub on the proximal portion; introducing the distal portion into a body lumen within the patient's body; coupling a valve hub to the tubular member hub, the valve hub including a valve body including a plurality of ports; inserting a first instrument into a first port of the valve hub such that the first instrument passes through the tubular member lumen into the body lumen; and inserting a second instrument into a second port of the valve such that the second instrument passes through the tubular member lumen into the body lumen.

In accordance with another embodiment, an apparatus is provided for performing a medical procedure within a patient's body that includes a tubular member including a proximal portion, a distal portion sized for introduction into a body lumen, and a lumen extending between the proximal portion and an outlet in the distal portion; and a valve hub including a valve body including a distal end coupled to the proximal portion of the tubular member and a proximal end including a plurality of ports communicating with the tubular member lumen, each port including one or more seals therein for accommodating inserting a device into the respective port and the tubular member lumen while providing a substantially fluid-tight seal.

In accordance with still another embodiment, a method is provided for performing a medical procedure within a patient's body that includes introducing a distal portion of a tubular member into a body lumen within the patient's body; inserting a first instrument into a first port of a valve hub on a proximal portion of the tubular member such that the first instrument passes through the tubular member lumen into the body lumen; and inserting a second instrument into a second port of the valve hub such that the second instrument passes through the tubular member lumen into the body lumen. Optionally, the method may include coupling the valve hub to the proximal portion of the tubular member, e.g., before or after introducing the distal portion into the body lumen. Alternatively, the valve hub may be substantially permanently coupled to the tubular member proximal portion.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a perspective view of an exemplary embodiment of an apparatus including an introducer sheath, a multiple port valve hub connectable to a hub of the introducer sheath, and a dilator also connectable to the hub of the introducer sheath.

FIGS. 4A-4F are end views showing exemplary port configurations that may be provided for the valve hubs.

DETAILED DESCRIPTION OF THE EXEMPLARY EMBODIMENTS

Figure 2A:
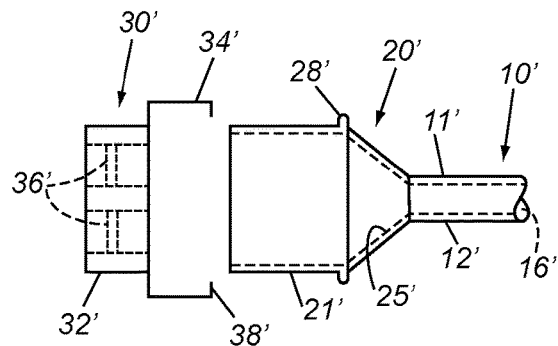
FIGS. 2A-2D are side view details of exemplary embodiments of cooperating connectors that may be provided for coupling the valve hub or dilator to the introducer sheath.

Turning to the drawings, FIG. 1 shows an exemplary embodiment of an apparatus 8 for accessing a body lumen (not shown) and/or delivering one or more instruments (also not shown) that includes an introducer sheath 10, a valve hub 30 removably connectable to the sheath 10, and optionally a dilator 50. Optionally, a plurality of valve hubs (not shown) may be provided that include different numbers and/or configurations of access ports to provide a system or kit in which any one of the valve hubs may be selectively and removably coupled to the introducer sheath 10, as described further elsewhere herein. Similarly, in another option, a plurality of dilators may be provided that include different configurations such that any one of the dilators may be selectively and removably coupled to the introducer sheath 10. The components of the apparatus 8 may be sized for introduction into a body lumen, such as a vessel within a patient's vasculature, a passage within a patient's gastrointestinal tract, urogenital tract, reproductive tract, respiratory tract, lymphatic system, and the like, e.g., for performing one or more medical procedures via the body lumen, as described further elsewhere herein.

Generally, the introducer sheath 10 includes an elongate tubular member 11 including a proximal end or portion 12, a distal end or portion 14 sized for introduction into a body lumen, a lumen 16 extending between the proximal and distal portions 12, 14 along a central longitudinal axis 18, and a handle or hub 20 on the proximal portion 12. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other medical device or instrument (not shown), and/or for delivering fluids or other flowable agents or materials therethrough, as described further below.

The tubular member 11 may be formed from a single piece of plastic or other material, e.g., by formed by extrusion, molding, and the like. Alternatively, the tubular body 11 may be constructed from one or more layers, e.g., an inner liner surrounding the lumen 16, a reinforcing layer surrounding the inner liner (not shown), and an outer layer. Optionally, one or more coatings, e.g., a lubricious coating (not shown), may be applied to the inner surface of the lumen 16, e.g., to facilitate introducing one or more instruments through the lumen 16.

In exemplary embodiments, the tubular body 11 may have an inner diameter between about twenty and seventy millimeters (20-70 mm) and/or an outer diameter between about twenty four and eighty millimeters (24-80 mm) corresponding to a inner sheath diameter of 6-24 Fr, and a length between about ten and one hundred fifty centimeters (10-50 cm) or between about twelve and thirty five centimeters (12-35 cm). For example, the tubular body 11 may be sized to extend from a percutaneous entry site in a patient's skin through the intervening tissue into a blood vessel, e.g., such that the distal portion 14 extends a relatively short distance into the vessel to provide access into the vessel, e.g., similar to a conventional introducer sheath. Alternatively, the tubular body 11 may be sized to extend from the entry site to a target location for performing a medical procedure within the patient's body, e.g., similar to a guide sheath.

The tubular member 11 may have a substantially homogenous construction between the proximal and distal portions 12, 14. Alternatively, the construction may vary along the length of the apparatus 10 to provide desired properties. For example, the proximal portion 12 may be substantially rigid or semi-rigid, e.g., providing sufficient column strength to facilitate advancing the introducer sheath 10 from the proximal portion 12, while the distal portion 14 may be substantially flexible or semi-rigid, e.g., to allow the distal portion 14 to bend easily or otherwise be advanced through tortuous anatomy with minimal risk of puncturing or otherwise damaging the vessel. Optionally, the distal portion 14 may include a tapered, rounded, or otherwise shaped distal tip, e.g., to provide a substantially atraumatic tip and/or to facilitate advancement or navigation.

Returning to FIG. 1, an exemplary embodiment of a sheath hub 20 is shown that includes a hub body 21 including proximal and distal ends 22, 24, a side port 23, a passage 25 extending between the proximal and distal ends 22, 24, and a valve 26 on or within the proximal end 22. The distal end 24 may be substantially permanently attached to the proximal portion 12 of the tubular member 11, e.g., by one or more of bonding with adhesive, sonic welding, interference fit, one or more connectors, and the like (not shown).

The valve 26 may include one or more conventional hemostatic valves that provide a substantially fluid-tight seal to prevent substantial flow of blood or other fluids proximally from the tubular member lumen 16 through the passage 25 and out the proximal end 22. For example, the valve 26 may include a component that provides a seal when the valve 26 is closed (before any instruments are introduced into the passage 25) and another component that provides a seal when one or more instruments are introduced into the passage 25. Exemplary embodiments of valves that may be provided are disclosed in U.S. Pat. Nos. 4,932,633, 5,098, 393, and 7,621,894, and U.S. Publication Nos. 2002/0007152 and 2009/0157006, the entire disclosures of which are expressly incorporated by reference herein.

The side port 23 may include additional conventional components, e.g., a length of flexible tubing 23a and a stopcock or other valve 23b for coupling other components to the sheath 10. In exemplary embodiments, the stopcock 23b includes one or more connectors, e.g., male or female Luer fittings to allow additional devices to be coupled to one or more ports on the stopcock 23b. For example, a source of saline or other fluid, e.g., a syringe (not shown), may be coupled to the stopcock 23b to infuse fluid through the side port 23 into the passage 25 and lumen 16, e.g., around one or more instruments introduced into the passage 25 and lumen 16. In addition or alternatively, a pressure sensor (also not shown) may be coupled to the stopcock 23b to measure blood pressure within a vessel within which the distal portion 14 is introduced.

In addition, the sheath hub 20 includes one or more connectors 28 on the hub body 21, e.g., for coupling the valve hub 30 and/or dilator 50 to the introducer sheath 10, as described elsewhere herein. In the exemplary embodiment shown, the connector(s) 28 include one or more external threads on the proximal end 22. Alternative embodiments of connectors that may be provided instead are shown in FIGS. 2A-2D, e.g., one or more snap connectors or other detents, and described further elsewhere herein.

Figure 3A:
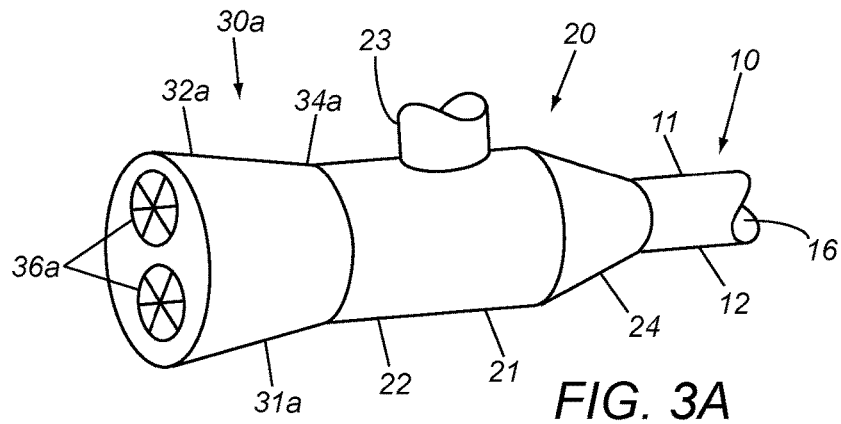
FIGS. 3A-3C are perspective views of exemplary embodiments of valve hubs coupled to the hub of an introducer sheath.
Figure 3B:
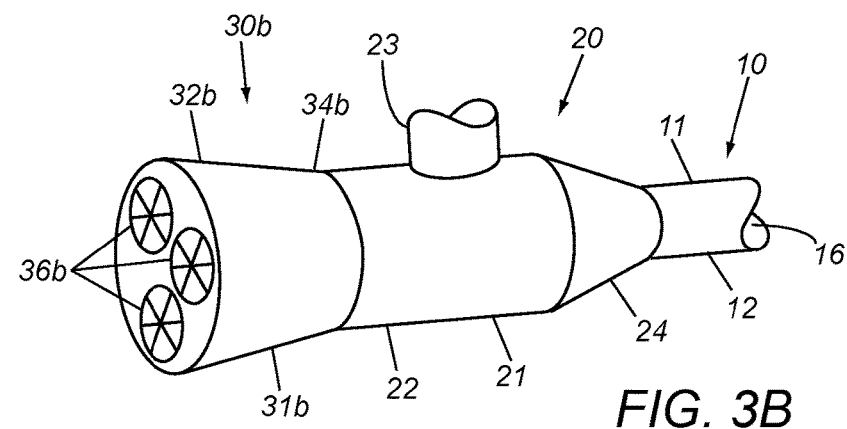
Figure 3C:
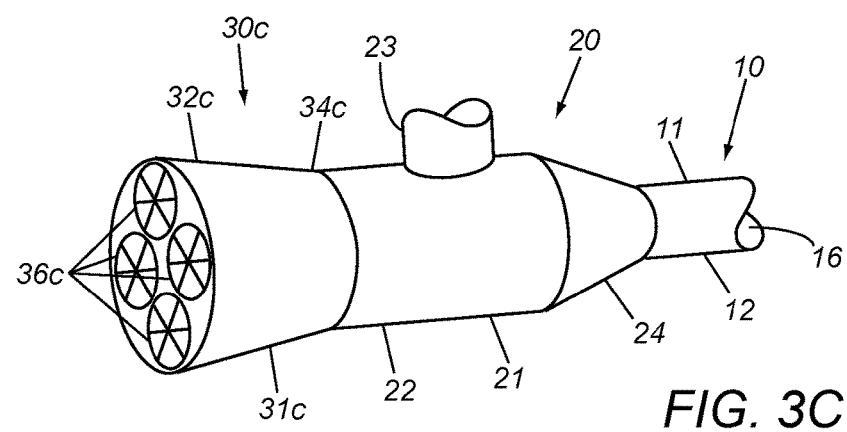

Returning to FIG. 1, an exemplary embodiment of a valve hub 30 is shown that generally includes a valve body 31 including a proximal or first end 32, a distal or second end 34, and a valve passage 35 extending between the first and second ends 32, 34. As shown, the valve body 31 and valve passage 35 may have a substantially uniform diameter or other cross-section between the first and second ends 32, 34. Alternatively, as shown in FIGS. 3A-3C, the valve body 31a-31c (and passage therein, not shown) may have a tapered shape, e.g., such that the second end 34a-34b has a diameter or other cross-section corresponding to the proximal end 22 of the sheath hub 20 and the first end 32a-32c has a larger diameter or other cross-section. Further, although the valve bodies 31-31c are shown as have a substantially circular cross-section (whether uniform or tapering along its length), the valve body may have other cross-sections. For example, the first end may have an elliptical or other geometric cross-section, e.g., to accommodate providing a desired number and/or configuration of access ports thereon, as described further elsewhere herein.

Returning to FIG. 1, the valve hub 30 includes a plurality of access ports 36 in the first end 32 communicating with the valve passage 35. The access ports 36 may extend only partially into the valve body 31 from the first end 32, e.g., such that the valve passage 35 has a single opening at the second end 34. Alternatively, the access ports 36 may extend entirely between the first and second ends of the valve body (not shown).

In the exemplary embodiment shown in FIGS. 1 and 3A, the valve hub 30 includes a pair of access ports 36, although alternatively, the valve hub 30 may include other numbers of access ports, e.g., three or four access ports 36b, 36c, as shown in FIGS. 3B and 3C, respectively. Additional alternatives are shown in FIGS. 4A-4F, e.g., including between one and six access ports. It will be appreciated that additional access ports may be provided if desired. Alternatively, it will be appreciated that other numbers of access ports may be provided and/or that the access ports may be arranged on the proximal end of the valve hub in various configurations.

In addition or alternatively, the access ports may have different sizes, e.g., diameters, to accommodate receiving instruments of various corresponding sizes. For example, as shown, the access ports 36a-36e on each valve hub 30a-30e may have the same diameter and/or size. Alternatively, one or more of the access ports 36a-36e may have a different size (not shown), e.g., such that each may accommodate different size catheters or other instruments (not shown). For example, in exemplary embodiments, the size of the access ports may correspond to the size of the introducer sheath. For example, for an 8 Fr (French=⅓ mm) sheath, a pair of access ports no larger than 4 Fr may be provided, while for a 9 Fr sheath, a 4 Fr and a 5 Fr access ports may be provided. In other examples, for a 10 Fr sheath, a pair of access ports may be provided that are both 5 Fr or one 4 Fr and one 6 Fr; for an 11 Fr sheath, a pair of access ports may be provided that are 4 Fr and 7 Fr, or 5 Fr and 6 Fr; for a 12 Fr sheath, a pair of access ports may be provided that are 4 Fr and 8 Fr or both 6 Fr; for a 14 Fr sheath, a pair of access ports may be provided that are 4 Fr and 10 Fr or 5 Fr and 9 Fr.

Each of the access ports 36 may include one or more valve components therein, e.g., to provide a substantially fluid-tight seal to prevent substantial fluid flow from the valve passage 35 through the first end 32, yet receive one or more instruments. For example, similar valve components may be provided in each valve port 36 similar to those described above with respect to the sheath hub 20.

In addition, the valve hub 30 also includes one or more connectors 38 for cooperating with the connector(s) 28 on the sheath hub 20. For example, in the embodiment shown in FIG. 1, one or more internal threads 38 may be provided in the second end 34 of the valve body 31. Thus, in this embodiment, the second end 34 of the valve hub 30 may be threaded over the proximal end 22 of the sheath hub 20, thereby coupling the valve hub 30 to the introducer sheath 10. Alternatively, internal threads may be provided on the sheath hub and external threads may be provided on the valve body such that the valve hub is threaded into the sheath hub (not shown).

FIGS. 2A-2D show other alternative connectors that may be provided on the valve hub and sheath hub. For example, FIG. 2A shows a sheath hub 20' that includes one or more external snap connectors or detents 28' and a valve hub 30' that includes one or more corresponding internal snap connectors or detents 38.' In exemplary embodiments, the detents 28,' 38' may extend continuously around the periphery of the sheath hub 20' and the second end 34' of the valve hub 30' although alternatively, a plurality of detents 28,' 38' may be provided spaced apart from one another circumferentially.

Figure 2B:
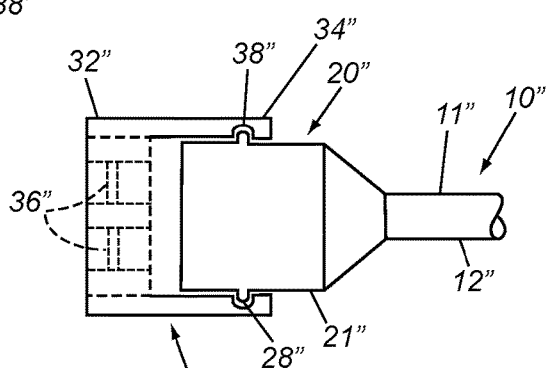
Figure 2C:
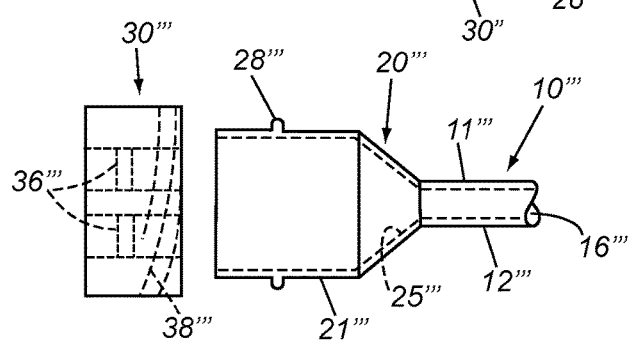

Alternatively, as shown in FIG. 2B, the sheath hub 20" may include one or more corresponding tabs 28" on the proximal end 22" and the valve hub 30" may include one or more recesses 38" within the second end 34." For example, the tab 28" may be a continuous annular tab and the recess 38" may be a similarly shaped continuous annular recess, or a plurality of similarly located tabs and recesses may be provided.

Figure 2D:
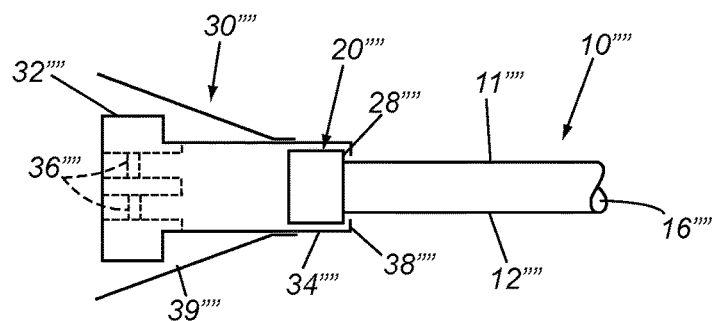

In a further alternative shown in FIG. 2D, a mechanical lever 39"" may be provided on the valve hub 30"" that is coupled to detents 38"" on the second end 34"" of the valve hub 30"". For example, the lever 39"" may be actuated to separate the detents 38"" from one another and allow the second end 34"" to be passed at least partially over the sheath hub 20"" until the detents 38"" are past the detents 28"" on the sheath hub 20"" (or aligned with recess detents, not shown) on the sheath hub 20."" Once the detents 28"", 38"" are aligned with one another, the lever 39"" may be released or otherwise actuated to engage the detents 28"", 38"", thereby coupling the valve hub 30"" to the sheath hub 20"".

Returning to FIG. 1 (although equally applicable to any of the embodiments herein), optionally, the valve hub 30 and/or sheath hub 20 may include one or more seals (not shown) to provide a substantially fluid-tight seal adjacent the cooperating connectors 28, 36 to prevent fluid from leaking once the valve hub 30 is fully threaded onto the sheath hub 20. For example, an O-ring (not shown) may be provided on one of valve hub 30 and the sheath hub 20 to provide a seal. Alternatively, the threads themselves may sufficiently engage one another to prevent fluid from leaking between the valve hub 30 and the sheath hub 20.

Although only a single modular valve hub 30 is shown in FIG. 1, it will be appreciated that a plurality of valve hubs 30 may be provided as a kit, e.g., each having different numbers, sizes, and/or configurations of access ports 36. For example, the kit may include a set of valve hubs 30 that include one, two, three, four, five, and six (or more) access ports. Optionally, the kit may also include valve hubs 30, each having different size access ports for different maximum size instruments. Alternatively, a plurality of introducer sheaths may be provided with each introducer sheath including a plurality of access ports in the sheath's hub (not shown). For example, the introducer sheaths may include different numbers and/or configurations of access ports such that a desired introducer sheath may be selected that provides a desired number and/or configuration of access ports for a particular procedure.

In another option, multiple introducer sheaths (not shown) may be included in the kit, e.g., providing different sizes of sheath lumens and/or outer profiles or lengths. Each of the sheaths in the kit may include a sheath hub having the same size proximal end and connectors, e.g., such that any of the valve hubs may be selectively coupled to any of the introducer sheaths. Alternatively, the introducer sheaths may have different size sheath hubs, e.g., larger hubs for larger diameter introducer sheaths, and different sets of valve hubs may be provided sized to couple to respective introducer sheaths.

Thus, the user may select a valve hub from the kit and couple it to an introducer sheath before or during a medical procedure. For example, in the embodiment shown in FIG. 1, the second end 34 of a selected valve hub 30 may be threaded onto the proximal end 22 of the sheath hub 20 of a selected introducer sheath 10. At any time, the valve hub 30 may be removed and replaced with a different valve hub, e.g., to provide an introducer sheath with a different number and/or configuration of access ports.

Returning to FIG. 1, in another option, one or more dilators 50 may be provided, e.g., as part of a kit. The exemplary dilator 50 shown includes an elongate tubular body 51 having a proximal portion 52, a distal portion 54, and a lumen 56 extending therebetween. A dilator hub 60 is provided on the proximal portion 52 that includes one or more connectors 58, e.g., internal threads or other connectors corresponding to the connector(s) on the sheath hub 20 of the introducer sheath 10. The dilator 50 may be manufactured using similar methods and materials to the introducer sheath 10, as described elsewhere herein.

The dilator tubular body 51 may have a predetermined length relative to the tubular member 11 of the introducer sheath 10, e.g., such the dilator distal portion 54 extends a predetermined distance from an outlet 15 of the introducer sheath 10 when the connectors 28, 58 are fully engaged. The dilator tubular body 51 has an outer diameter or cross-section corresponding to the lumen 16 of the introducer sheath 10 such that the dilator 50 may be inserted into the introducer sheath 10 freely with minimal lateral movement.

If multiple introducer sheaths are provided that have different lengths, a set of corresponding dilators may also be provided. In addition or alternatively, multiple dilators may be provided having different size lumens. For example, the dilator 50 may include a lumen 56 having a diameter for slidably receiving a guidewire (not shown) therethrough, e.g., having a diameter between about 0.014-0.018 inch, e.g., such that the dilator 50 may be advanced over a guidewire placed into the patient's body, as described elsewhere herein.

In addition or alternatively, one or more dilators may be provided that include other size lumens, e.g., having a diameter between about 0.035-0.050 inch (0.875-1.25 mm), e.g., for receiving a needle (not shown) therethrough such that the needle and dilator may be penetrated into tissue together, also as described further elsewhere herein. In yet another alternative, multiple dilators may be provided that may be advanced over one another, e.g., to provide desired dilation configurations for dilating tissue during placement of the introducer sheath 10.

During use, the apparatus 8 may be used for introducing a plurality of medical devices or instruments into a body lumen within a patient's body, e.g., one or more catheters and the like, into a patient's vasculature or other body lumen, as described above. In exemplary embodiments, the apparatus 8 and kits herein may be used during a variety of procedures that involve introducing and/or manipulating two or more instruments in conjunction with one another, such as electrophysiology procedures, such as mapping and/or ablation procedures; balloon aortic valvuloplasty (BAV) or trans-catheter aortic valve replacement (TAVR) procedures involving multiple venous sheaths, e.g., where temporary pacing, hemodynamics, CO, and/or cardiopulmonary bypass may be needed simultaneously, pacing lead placement procedures; patients in ICUs, CCUs, and the like who require hemodialysis, hemodynamic monitoring, and/or pacing; foreign body retrieval procedures; and other conventional procedures involving multiple access sites.

For example, a conventional TAVR procedure may involve up to five arterial introducer sheaths and three venous introducer sheaths (e.g., eight total), to accommodate an arterial line, a TAVR sheath, two angiographic catheters, cardiopulmonary bypass, temporary pacing, hemodynamic monitoring, and optionally embolic protection devices. The apparatus 8 may allow only two introducer sheaths to be used, e.g., one accessing the arterial system and one accessing the venous system of the patient yet allow introduction of all of the desired catheters and instruments.

Initially, the introducer sheath 10 may be introduced into a patient's vasculature, e.g. in conjunction with the dilator 50. For example, a hollow needle (not shown) may be inserted through a patient's skin and overlying tissue into a target blood vessel, e.g., a femoral artery or vein, a carotid artery, and the like. A guide wire (also not shown) may be passed through the needle lumen into the blood vessel, whereupon the needle may be removed.

The dilator 50 may be inserted into the lumen 16 of the introducer sheath 10 and the connectors 28, 58 engaged, e.g., such the dilator distal portion 54 extends from the sheath distal portion 14 to provide a desired transition. For example, if multiple size introducer sheaths and dilators are provided as part of a kit, the desired configuration may be identified based on the patient's anatomy and/or the intended procedure, and an appropriate introducer sheath 10 and dilator 50 may be selected and coupled together.

The guidewire may then be backloaded into the dilator distal portion 54 through the dilator lumen 56 and then the sheath 10 and dilator 50 may be advanced together over the guidewire through the patient's skin, intervening tissue, and into the vessel. In an alternative procedure, the sheath 10 and dilator 50 may be loaded onto a needle (not shown, and the resulting assembly may be penetrated directly into the patient's skin and through the intervening tissue into the vessel. The guidewire or needle may then be removed and then the dilator 50 may be uncoupled and removed, leaving the introducer sheath 10 in position providing access into the vessel. In an alternative embodiment, the guidewire may remain within the introducer sheath 10 and the dilator 50 may be removed over the guidewire, e.g., such that the guidewire may be used to introduce additional devices through the introducer sheath 10. As with conventional introducer sheaths 10, the valve 26 within the sheath hub 20 may provide a substantially fluid-tight seal to prevent blood from leaking from the vessel through the introducer sheath 10.

With the introducer sheath 10 positioned within the vessel, a valve hub 30 may be selected, e.g., that provides a desired number and/or configuration of access ports 36, and coupled to the sheath hub 20, e.g., by engaging the connectors 28, 38, as described elsewhere herein. A guidewire (not shown) may then be introduced into each of the access ports 36 and advanced through the patient's vasculature to one or more target locations.

One or more catheters or other instruments (not shown) may then be introduced over respective guidewires into respective access ports 36 and advanced to the target location(s), e.g., to perform a desired procedure, such as those described elsewhere herein. The seal(s) within the access ports 36 may allow the instruments to be introduced through the introducer sheath 10 and manipulated while providing a substantially fluid-tight seal around the instruments.

If at any time, additional access ports are desired than are provided by the coupled valve hub 30, the valve hub 30 may be uncoupled from the introducer sheath 10, e.g., by disengaging the connectors 28, 38, and selecting another valve hub and coupling it to the introducer sheath. During such an exchange, the instruments introduced into the introducer sheath 10 may be removed before uncoupling the valve hub 30, e.g., while leaving the guidewires in place or the guidewires may also be approved. The new valve hub may be coupled to the introducer sheath and another set of instruments may be introduced into the patient's body via the access ports of the new valve hub.

Once the procedure is completed, the instruments and guidewires may be removed, and then the introducer sheath 10 may be removed. The remaining puncture may then be sealed using conventional methods. Thus, one advantage of the apparatus and methods herein is that fewer punctures may be required that need to sealed upon completion of the procedure, which may facilitate patient recovery, e.g., as compared to procedures requiring many separate punctures.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for performing a medical procedure within a patient's body, comprising:
   a tubular member comprising a proximal portion, a distal portion sized for introduction into a body lumen, a lumen extending between the proximal portion and an outlet in the distal portion, and a hub on the proximal portion including a passage communicating between a hub proximal end and the tubular member lumen and one or more hemostatic valves in the hub that provide a substantially fluid-tight seal to prevent substantial flow of fluids proximally from the tubular member lumen through the passage and out the hub proximal end and accommodate introducing one or more instruments into the passage;

a valve member separate from the hub comprising a valve body including a proximal end and a distal end, a plurality of ports on the proximal end communicating with a single opening in the distal end, each port comprising one or more seals therein for accommodating inserting a device into the port while providing a substantially fluid-tight seal; and cooperating connectors on one or both of the hub proximal end and the valve body for releasably coupling the valve body to the hub proximal end such that the device inserted into one of the ports passes through the passage and enters the tubular member lumen.

2. The apparatus of claim 1, wherein the cooperating connectors comprise mating threads on the valve body and the tubular member hub configured to allow the valve body to be threaded onto the tubular member hub proximal end.

3. The apparatus of claim 1, wherein the cooperating connectors comprise mating detents on the valve body and the tubular member hub.

4. The apparatus of claim 1, further comprising a dilator that includes a proximal portion including a hub and a distal portion sized for insertion into the tubular member hub and lumen such that the distal portion extends from the outlet, the dilator hub including one or more connectors for engaging one or more connectors on the tubular member hub for coupling the dilator to the tubular member.

5. The apparatus of claim 4, wherein the dilator distal portion comprises a tapered tip that extends from the outlet when the dilator is coupled to the tubular member to provide a substantially atraumatic transition to the tubular member distal portion.

6. The apparatus of claim 1, wherein the valve member includes two ports.

7. The apparatus of claim 1, wherein the tubular member hub comprises a side port communicating with the passage and tubing extending from the side port to a stopcock for infusing fluid into the passage and tubular member lumen.

8. The apparatus of claim 1, wherein the tubular member has a length between ten and fifty centimeters (10-50 cm) and a diameter between six and twenty four French (2-8 mm).

9. The apparatus of claim 1, wherein the valve body has an annular shape including a proximal surface comprising the plurality of ports therein, and wherein each of the plurality of ports comprises one or more valve components providing the one or more seals.

10. A kit for performing a medical procedure, comprising:
a tubular member comprising a proximal portion, a distal portion sized for introduction into a body lumen, a lumen extending between the proximal portion and an outlet in the distal portion, and a hub on the proximal portion including one or more hemostatic valves therein;
a plurality of valve hubs separate from the hub, each valve hub comprising a valve body including a proximal end and a distal end, a plurality of ports on the proximal end communicating with a single opening in the distal end, each port comprising one or more seals therein for accommodating inserting a device into the port while providing a substantially fluid-tight seal; and a dilator comprising a proximal portion including a hub and a distal portion sized for insertion into the tubular member hub and lumen such that the dilator distal portion extends from the outlet, wherein each valve hub and the dilator comprises one or more connectors for mating with one or more connectors on the tubular member hub for releasably coupling a selected valve hub or the dilator to the tubular member hub.

11. The kit of claim 10, wherein each of the plurality of valve hubs has a different number of ports.

12. The kit of claim 10, wherein at least one of the valve hubs has a port with a different diameter than a port of another of the valve hubs.

13. The kit of claim 10, wherein at least one of the valve hubs has two ports and at least one of the valve hubs has three ports.

14. The kit of claim 10, wherein the one or more connectors comprise one or more mating threads on the valve body for engaging one or more mating threads on one of the valve hubs and the dilator.

15. The kit of claim 10, wherein the dilator is a first dilator comprising a first lumen extending between the first dilator proximal and distal portions, the kit further comprising a second dilator comprising a proximal portion including a hub and a distal portion sized for insertion into the tubular member hub and lumen such that the distal portion extends from the outlet, the second dilator comprising a second lumen extending between the second dilator proximal and distal portions, the second lumen having a different size than the first lumen.

16. The kit of claim 10, wherein the tubular member has a length between ten and one hundred fifty centimeters (10-50 cm) and a diameter between six and twenty four French (2-8 mm).

17. An apparatus for introducing multiple instruments into a patient's vasculature, comprising:
a tubular member comprising a proximal portion, a distal portion sized for introduction into the patient's vasculature, a lumen extending between the proximal portion and an outlet in the distal portion, the tubular member having a length between ten and fifty centimeters (10-50 cm) and a diameter between six and twenty four French (2-8 mm);
a hub including proximal and distal ends and a passage extending between the hub proximal and distal ends, the hub distal end permanently attached to the tubular member proximal portion such that the passage communicates with the tubular member lumen;
one or more hemostatic valves within the hub that provide a substantially fluid-tight seal to prevent substantial flow of blood or other fluids proximally from the tubular member lumen through the passage and out the proximal end and accommodate introducing one or more instruments into the passage;
a valve member separate from the hub comprising a valve body including a proximal end and a distal end, a plurality of ports on the proximal end communicating with a single opening in the distal end, each port comprising one or more seals therein for accommodating inserting a device into the port while providing a substantially fluid-tight seal; and
cooperating connectors on the tubular member hub and the valve body for releasably coupling the valve member to the hub proximal end such that the device inserted into one of the ports passes through the passage and enters the tubular member lumen.

18. The apparatus of claim 17, wherein the hub comprises a side port communicating with the passage and tubing extending from the side port to a stopcock for infusing fluid into the passage and tubular member lumen.

19. The apparatus of claim 17, wherein the distal portion comprises a tapered distal tip to facilitate advancement of the distal portion within a body lumen.

* * * * *